United States Patent
Holloway et al.

(10) Patent No.: US 7,304,201 B2
(45) Date of Patent: Dec. 4, 2007

(54) PHOTOTHERAPY BANDAGE

(75) Inventors: Paul H. Holloway, Gainesville, FL (US); Gary McGuire, Chapel Hill, NC (US); Olga A. Shenderova, Raleigh, NC (US); John Reynolds, Gainesville, FL (US); Kirk S. Schanze, Gainesville, FL (US); James Boncella, Los Alamos, NM (US)

(73) Assignees: University of Florida Research Foundation, Inc., Gainesville, FL (US); International Technology Center, Raleigh, NC (US)

( * ) Notice: Subject to any disclaimer, the term of this patent is extended or adjusted under 35 U.S.C. 154(b) by 724 days.

(21) Appl. No.: 10/732,086

(22) Filed: Dec. 10, 2003

(65) Prior Publication Data

US 2004/0166146 A1    Aug. 26, 2004

Related U.S. Application Data (63) Continuation-in-part of application No. 10/170,942, filed on Jun. 12, 2002.

(60) Provisional application No. 60/432,284, filed on Dec. 10, 2002.

(51) Int. Cl.
*A61F 13/00* (2006.01)
(52) U.S. Cl. .............. 602/41; 602/42; 607/88
(58) Field of Classification Search ......... 602/41, 602/42; 607/88, 89, 91
See application file for complete search history.

(56) References Cited

U.S. PATENT DOCUMENTS

| | | | |
|---|---|---|---|
| 5,795,286 A | 8/1998 | Fischell et al. | |
| 6,045,575 A | 4/2000 | Rosen et al. | |
| 6,096,066 A * | 8/2000 | Chen et al. | 607/88 |
| 6,156,028 A | 12/2000 | Prescott | |
| 6,290,713 B1 * | 9/2001 | Russell | 607/88 |
| 6,454,791 B1 | 9/2002 | Prescott | |
| 6,860,896 B2 * | 3/2005 | Leber et al. | 607/1 |
| 6,866,678 B2 | 3/2005 | Shenderova et al. | |
| 7,070,611 B2 * | 7/2006 | Biel | 607/88 |
| 2001/0030325 A1 | 10/2001 | Epstein | |
| 2001/0047144 A1 * | 11/2001 | Tillotson et al. | 602/41 |

* cited by examiner

*Primary Examiner*—Michael A. Brown
(74) *Attorney, Agent, or Firm*—Akerman Senterfitt; Gregory A. Nelson; Michael K. Dixon

(57) ABSTRACT

A phototherapy bandage capable of providing radiation to a localized area of a patient for accelerating wound healing and pain relief, photodynamic therapy, and for aesthetic applications. The phototherapy bandage may include a flexible light source that is continuous across the bandage for providing a selected light, such as a visible light, a near-infrared light, or other light, having substantially similar intensity across the bandage. The bandage may also be flexible and capable of being attached to a patient without interfering with the patient's daily routine. The phototherapy bandage may easily conform to the curves of a patient and may come in a variety of exterior shapes and sizes.

37 Claims, 5 Drawing Sheets

MEH-PPV

FIG. 3

Ln=Yb³⁺ or Er³⁺
Ln(TPP)acac

PHOTOTHERAPY BANDAGE

CROSS-REFERENCE TO RELATED APPLICATION

This application claims the benefit of U.S. Provisional Application No. 60/432,284, filed Dec. 10, 2002, and is a continuation-in-part of U.S. patent application Ser. No. 10/170,942, filed Jun. 12, 2002.

FIELD OF THE INVENTION

The invention is directed generally to phototherapy, and more particularly, to methods and devices for administering radiation to a targeted site on a patient.

BACKGROUND

Phototherapy is the therapeutic use of light that has been recognized as an effective method of treating wounds and reducing pain in humans. External phototherapy has been effective in treating various medical conditions, such as, but not limited to, bulimia nervosa, herpes, psoriasis, seasonal affective disorder, sleep disorders, acne, skin cancer, hyperbilirubinemia in infants, and other conditions. Phototherapy is typically administered to a patient using a light source consisting of either a bank of lights, referred to as a light bank, or a fiber optic light source. Some of the first phototherapy light sources included light banks positioned over incubators or open bassinets, or under hoods or transparent supports. Typically, the light sources used in phototherapy consist of fluorescent tubes, metal halide lamps, or light-emitting diodes (LEDs).

While light sources having light banks are still being used, such devices are not without their disadvantages. For instance, phototherapy devices using light banks require that patients wear eye protection that is often uncomfortable. These devices also require that patients remain relative stationary while receiving treatment. Furthermore, these devices are typically large and immobile, which thus, require patients to visit the locations of the light sources each time a dosage is needed. Light sources using light banks are disadvantageous for at least these reasons.

Fiber optic light sources were developed as a substitute for phototherapy devices containing light banks but have not eliminated all of the drawbacks associated with these devices. For instance, while the fiber optic lights are more mobile than light bank devices, the fiber optic lights typically deliver lower overall amounts of light than the light banks. Additionally, fiber optic lights are often used in conjunction with fiber optic mats having specific geometries. Often times, the geometries of the fiber optic mats are compromised when forces are placed on the fiber optic mats in order to place the fiber optic mats in contact with patients' skin surfaces. This undesirably results in greater light intensity being concentrated near the light source than at other portions of the fiber optic mat.

LEDs are typically used as light sources for phototherapy. For instance, U.S. Pat. Nos. 6,290,713 and 6,096,066 describe flexible mats having a plurality of LEDs positioned in arrays that are coupled to a plurality of conductive traces for emitting light. The LEDs are point sources that do not emit light over a broad area, but rather over a narrow area. Light produced by the LEDs is diffused and made more uniform by placing diffusers in the mats near the LEDs. Without the diffusers, the arrays of LEDs are simply collections of point sources. Because diffusers are used, the LEDs cannot be placed in contact with a surface. Instead, the thickness of the diffuser limits the proximity with which the LEDs may be positioned proximate to a surface. Thus, the amount of light that an LED emits is not the same amount of light that reaches the surface because a portion of the light produced by the LED is lost when the LED is not placed in contact with a surface.

LEDs produce a single wavelength of light. If more than one wavelength of light is required, more than one type of LED must be used. In order to operate the LEDs, the mats contain numerous conductors to provide power to each LED individually. These conductors significantly add to the overall weight and complexity of the mats.

The mats are made even more complex with the addition of channels for dissipating heat. Use of the plurality of LEDs in such close proximity to each other produces high amounts of heat that can pose potentially dangerous conditions. This heat is typically vented from the devices using channels between the LEDs. While the channels do allow a portion of the heat produced by the LEDs to be vented from the mat, not all of the heat generated is removed.

Thus, a need exists for a phototherapy device that delivers light in a more efficient manner while retaining the advantages of a flexible mat.

SUMMARY OF THE INVENTION

According to one aspect of this invention, the phototherapy bandage is a self-contained device that is formed from a base and at least one light source for emitting radiation and directing it toward a targeted location on a patient, which is defined to be a human or an animal. In at least one embodiment, the phototherapy bandage is flexible and capable of conforming to a patient, and more specifically, is capable of being coupled to an exterior skin surface of a patient. In one embodiment, the light source may be an electroluminescent (EL) device, which may be an organic or inorganic electroluminescent device.

The EL device may be capable of emitting radiation at different wavelengths, such as all wavelengths forming visible light, including red light, near-infrared radiation (NIR or near-IR), and mid-infrared radiation. The EL device is capable of providing illumination within a limited wavelength range to a target area from one to tens of square centimeters. The EL light source can be tailored to emit wavelengths from visible light to near-infrared light by co-doping or by using multilayered EL structures. A single EL light source can be used to treat a range of conditions and can be fabricated to control flux and dose.

The EL light source may be coupled to the base using any connection mechanism, and in one embodiment, the base may be coupled to at least one light source using an adhesive. The adhesive may also be used to couple the phototherapy bandage to a patient. The base may also include a moisture barrier for preventing moisture from contacting the light source.

The phototherapy bandage may also include one or more batteries, which may or may not be rechargeable, for powering the light source. The phototherapy bandage may further have one or more microprocessors for controlling operation of the light source. The microprocessor may operate the light source continuously or intermittently depending on a variety of factors. The phototherapy bandage may further include a moisture barrier positioned on the light source to prevent the light source, the microprocessor, and the battery from contacting a fluid. The phototherapy bandage may be used for aesthetic applications and for photodynamic therapy.

An advantage of this invention is that the phototherapy bandage is flexible and capable of being attached to a patient to accelerate wound healing and providing pain relief without interfering with the patient's daily activities.

Another advantage of this invention is that the light source is capable of being extended across the healing area of the bandage so that when used the selected wavelength of light, which may be, visible light, near-IR light, or longer wavelength IR light, may be emitted in a relatively uniform manner towards the intended healing surface.

Another advantage of this invention is that the phototherapy bandage is a self-contained device that is easy to carry and wear.

Yet another advantage of this invention is that the phototherapy bandage may be self-applied by the patient.

Another advantage of this invention is that the phototherapy bandage is portable and is relatively small, which enables the bandage to be packed in various hand bags, backpacks, hiking equipment, luggage and other storage devices.

Still another advantage of this invention is that the phototherapy bandage may be contained in a moisture resistant package and applied to a patient when necessary.

Another advantage of this invention is that the phototherapy bandage may be used for a relatively long duration when used with rechargeable batteries.

Yet another advantage of this invention is that the EL source is capable of emitting both visible and NIR wavelengths.

Another advantage of this invention is that the EL source can emit multiple NIR wavelengths at wavelengths that are known to have therapeutic benefits in wound healing and pain relief.

Still another advantage of this invention is that the EL source may be formed from one or more layers or pixels that allow sequential or simultaneous emission of light at different wavelengths.

Another advantage of this invention is that the EL source is capable of operating at or below freezing temperatures.

Yet another advantage of this invention is that the EL source may be operated using low voltage.

Another advantage of this invention is that the EL source is capable of emitting a uniform emission without use of diffusers.

Another advantage of this invention is that the EL source is rugged and capable of absorbing the stresses commonly placed on a bandage.

These and other features and advantages of the present invention will become apparent after review of the following drawings and detailed description of the disclosed embodiments.

BRIEF DESCRIPTION OF THE DRAWINGS

The accompanying drawings, which are incorporated in and form a part of the specification, illustrate preferred embodiments of the presently disclosed invention(s) and, together with the description, disclose the principles of the invention(s). These several illustrative figures include the following.

DETAILED DESCRIPTION

The phototherapy bandage 10 of this invention is capable of providing radiation to a localized area of a patient, who may be a human or animal, for accelerating wound healing and pain relief. In addition, phototherapy bandage 10 may also be used for photodynamic therapy and for aesthetic applications. In one embodiment, phototherapy bandage 10 is flexible and capable of being attached to a patient without interfering with the patient's daily routine. Phototherapy bandage 10 may easily conform to the curves of a patient and may come in a variety of exterior shapes and sizes.

The term "phototherapy", as used herein is intended to embrace both phototherapy and photodynamic therapy. The term "infrared" as used herein is intended to encompass the range of light spectrum above approximately 650 nm and includes regions often termed "near-infrared" and includes "mid-infrared." "Transparency" as used herein is defined as passing a substantial portion of light at a wavelength of interest, while "reflectivity" is similarly defined as reflective of a substantial portion of light at a wavelength of interest. The term Thin Film Electroluminescence (TFEL) as used herein should be interpreted to mean electroluminescent (EL) devices that are made of stacked layers that are substantially planar in that the thickness of their essential light creation components is much smaller than their other dimensions. This term is intended to embrace inorganic high field EL devices as well as organic light emitting devices (OLEDs) (whether a dopant is used in the active layer or not), which can be made with major dimensions ranging from millimeters to several inches and beyond. The term TFEL specifically excludes conventional inorganic semiconductor laser and conventional inorganic semiconductor diode devices such as LEDs and LDs (which may broadly fall within certain definitions of EL sources). The term TFEL also clearly specifically excludes incandescent lamps, fluorescent lamps and electric arcs. The term EL as used herein, is generally intended to mean TFEL. The term "dopant" as used herein can mean a dopant atom (generally a metal) as well as metal complexes and metal-organic compounds used as an impurity within the active layer of a TFEL device. Some of the organic-based TFEL active layers may not contain dopants. The term LED as used herein is intended to mean conventional inorganic (e.g., doped compound semiconductor based) semiconductor light emitting diodes. The term "OLED" is intended to exclude such conventional inorganic semiconductor LEDs, even though an OLED is often referred to as a type of organic based light emitting diode.

Figure 1:
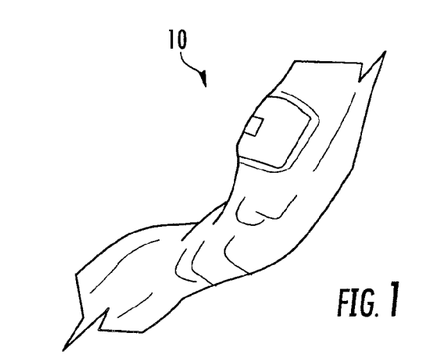
FIG. 1 is an artistic rendering of an exemplary embodiment of a phototherapy bandage.
Figure 2:
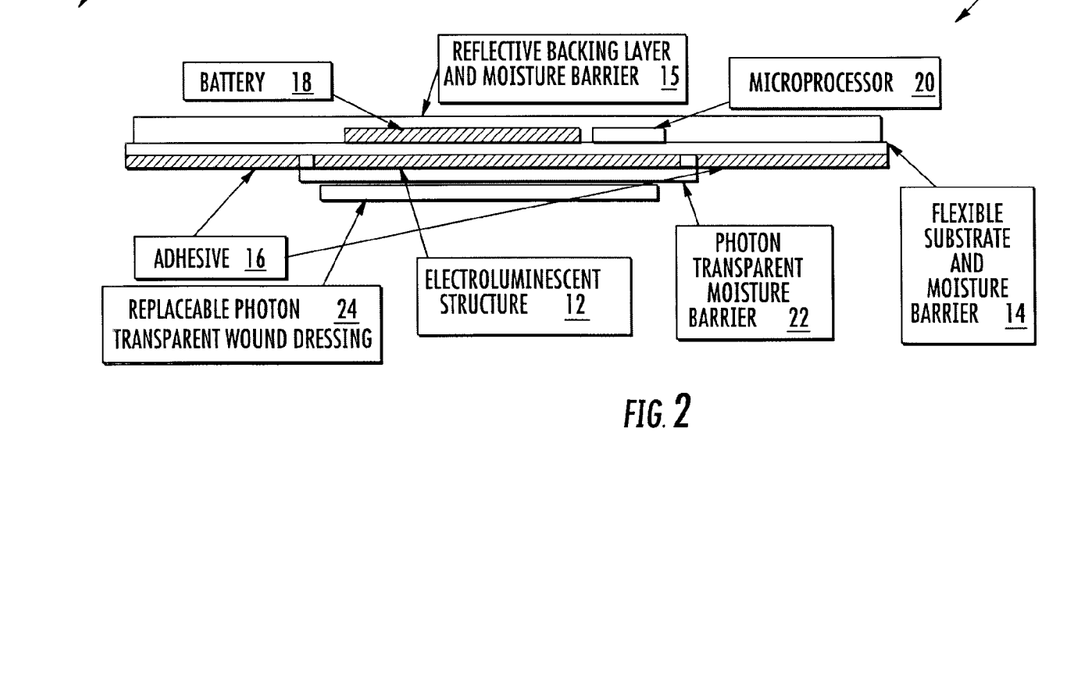
FIG. 2 is a schematic diagram of a side view of a phototherapy bandage of this invention.

In one embodiment, as shown in FIGS. 1 and 2, phototherapy bandage 10 is composed of one or more flexible light sources 12 that are coupled to a base 14. In at least one embodiment, a single light source 12 may be employed. Phototherapy bandage 10 may further include an adhesive 16 coupled to base 14 for attaching phototherapy bandage 10 to a patient. Phototherapy bandage 10 may also include a battery 18 and a microprocessor 20 that may control light source 12. Battery 18 may be coupled to microprocessor 20 using any conventional devices, such as, but not limited to, one or more insulated electrically conductive wires. Battery 18 may be a conventional battery that is rechargeable or not and sized proportionally to be attached to base 14, as shown in FIG. 2. Battery 18 may be flexible and may have a thickness of about 0.5 mm with 1.5 volts at 2.5 m Ah/cm$^2$. Multiple batteries may be used to achieve the desired voltage. Microprocessor 20 may be programmable and capable of controlling the operation of light source 12 in many ways. Microprocessor 20 may be integrated with a panel to select or set the optical protocols, which will allow different doses, frequencies and times of exposure.

In one or more embodiments, light source 12 may be a light source that is itself flexible and capable of emitting light in a substantially similar intensity across the bandage 10. For instance, the light source 12 may be, but is not limited to being, an electroluminescent device (EL) spread across a substantial portion of the base 14. The light source 12 may include only two electrodes that need to be connected to a battery 18, rather than the plurality of conductors used with arrays of LEDs. This minimal number of conductors used in this invention reduces manufacturing costs and complexity of the bandage 12 and enhances its reliability. In one embodiment, the light source 12 may be a thin film EL (TFEL) device. The EL light source 12 may be capable of emitting light at both visible and NIR wavelengths. In addition, light source 12 may be capable of emitting radiation substantially uniformly over a targeted area of a patient without the use of diffusers. The EL device may be configured to emit a single wavelength or multiple wavelengths of light. The EL device may have one or more layers capable of being activated separately or together and have compositions that produce two or more different emissions. The two or more layers may be turn on separately or simultaneously.

The EL device forming light source 12 may be an inorganic electroluminescent light source, as described in more detail below. For instance, the EL device may be formed from zinc sulfide doped with one or more lanthanide elements, such as, but not limited to, neodymium, samarium, terbium, dysprosium, holmium, erbium, thulium, and ytterbium. The inorganic EL may include a thin layer of zinc sulfide doped with a lanthanide sandwiched between two insulator films. The lanthanide concentration may be between about 0.1% and about 2.0%, and the two insulator films may be made of silicon oxynitride. The inorganic EL may include a reflecting electrode on a back surface of the device and a transparent electrode on the front surface of the device. The El device forming light source 12 may also be an organic light source such as, but not limited to, the light sources described in more detail below.

Base 14 may be configured to be attached to a patient and conform to the contours of the patient's outer skin surface or other surface. In another embodiment, base 14 is configured to be placed in close proximity to a patient, but not in contact with the patient. Base 14 may be any flexible material that is capable of conforming to the exterior shape of human and animal bodies and may include, but is not limited to, biocompatible polymers or plastics. Base 14 also forms an illuminating surface from which radiation leaves phototherapy bandage 10.

Phototherapy bandage 10 may include one or more barriers 15 attached to the top portion of base 14. Barrier 15 may prevent moisture from contacting battery 18 and microprocessor 20. In addition, barrier 15 may be reflective so that light produced by light source 12 is reflected and does not pass through barrier 15.

Adhesive 16 may be coupled to one or more sides of base 14. Adhesive 16 may be applied intermittingly or may be applied to cover an entire side of base 14. In one embodiment, adhesive 16 is applied in strips to base 14. Adhesive 16 may be any conventional adhesive and preferably has sufficient strength to keep phototherapy bandage 10 in contact with a patient while not having too much strength such that phototherapy bandage 10 cannot be removed from the patient. As shown in FIG. 2, adhesive 16 may be located between base 14 and light source 12.

Phototherapy bandage 10 may include a barrier 22 coupled to light source 12 for preventing moisture from contacting light source 12. Barrier 22 may be photon transparent. Phototherapy bandage 10 may include wound dressing 24 coupled to a bottom surface of the bandage 10. Wound dressing 24 may also be photon transparent and sterile.

Phototherapy bandage 10 may be coupled to a patient by another person or may be self-administered by the patient. In addition, phototherapy bandage 10 may be stored in a moisture resistant package that may be easily packaged together with a first aid kit or packaged separately for outdoorsmen and others.

During use, phototherapy bandage 10 is coupled to a surface of a patient. The patient may attach phototherapy bandage 10 to himself or herself, or phototherapy bandage may be attached by someone else. The phototherapy bandage 10 may be coupled to the wound site for any amount of time depending on whether the bandage is being used for pain relief or tissue healing. In one embodiment, phototherapy bandage 10 is attached to a skin surface from three to ten days. While phototherapy bandage 10 is attached to a patient, the bandage may emit light continuously or intermittently, or both. The therapy process may be controlled by microprocessor 20.

Electroluminescent Light Sources

The light source may be formed from electroluminescent materials capable of producing visible light, near-infrared (near-IR) radiation, and longer wavelength radiation, such as mid-infrared radiation. In at least one embodiment, the electroluminescent materials may be formed from a luminescent polymer and a metal containing compound where the metal containing compound incorporates a metal-ligand complex such that the absorption spectrum of the metal-ligand complex at least partially overlaps with the emission spectrum of the luminescent polymer. As the absorption spectrum of the metal-ligand complex at least partially overlaps with the emission spectrum of the luminescent polymer when the luminescent polymer becomes electronically excited, energy can be transferred from the luminescent polymer to the metal-ligand complex. At least a portion of the energy transferred from the luminescent polymer to the metal-ligand complex can then be emitted by the metal-ligand complex as near-infrared radiation. Conjugated polymers that are luminescent can be utilized.

In one embodiment, where the electroluminescent material may be a luminescent polymer and a metal-containing compound where the metal-containing compound incorporates a metal-ligand complex, the absorption spectrum of the ligand of the metal-ligand complex at least partially overlaps with the emission spectrum of the luminescent polymer such that when the luminescent polymer becomes electronically excited, energy is transferred from the luminescent polymer to the ligand. Energy can then be transferred from the ligand to the metal by sensitization. The energy transferred to the metal by sensitation may then be emitted as near-IR radiation or other radiation.

The energy transferred from the luminescent polymer to the metal-ligand complex or from the luminescent polymer to the ligand can be transferred by one or more mechanisms including, but not limited to, Förster transfer and/or Dexter transfer. The luminescent polymer can become electronically excited upon the creation of excitons in the luminescent polymer by, for example, the application of an electric current through the luminescent polymer and/or exposing the luminescent polymer to photons. Once created, the excitons within the luminescent polymer can be mobile within the luminescent polymer. At least a portion of these mobile excitons may then be trapped by the metal, or metal-ligand complex, within the luminescent polymer.

In another embodiment, the metal-containing compound can be a metal organic compound. In at least one embodiment, the metal-containing compound may include a lanthanide as the metal. The metal-containing compound that includes a lanthanide may also include one or more ligands, which may be, but is not limited to being, a macrocyclic chelator, which is strongly light absorbing. The metal compounds that may be used are metals that include lanthanides such as, but not limited to, $Yb^{+3}$, Dy, Nd, Ho, Pr, $Er^{+3}$, or Tm, sulfides, and halide compounds and complexes such as oxy-compounds. The metal compounds may also be oxomolybdenum(IV) complexes, such as $[MoOCL(CN\text{-}t\text{-}Bu)_4]^+$ and related compounds, or Pt—Pd stacked complexes such as $[Pt(NC—R)_4^{2+}, Pd(CN)_4^{2-}]$ and related compounds.

Ligands that may be utilized may include, but are not limited to, the entire family of light absorbing organic compounds that are known to bind to metal ions by chelation, coordinate covalent bonding, or other binding mechanisms. Specific examples include (1) tetraaryl porphyrins, wherein the aryl group may, or may not, be substituted with alkyl, alkyl ether, oligoether, alkyl sulfonate, alkyl amine, and/or other substituent groups or atoms, such as 5, 10, 15, 20-tetraphenylporphyrin, (2) octaalkyl porphyrins including octaethyl porphyrin, (3) chlorophyls, bacteriochlorophyls, chlorins, and other naturally and unnaturally occurring tetrapyrroler macrocycles, (4) texaphyins and related substituted and unsubstituted pentapyrrole macrocycles, (5) phthalocyanines, naphthophthalocyanines, and other structurally-related substituted and unsubstituted phthalocyanines.

Polymers that may be utilized may include, but are not limited to, the entire family of conjugated polymers including (1) those that are fully conjugated, (2) those that include broken links of conjugation, and (3) those that incorporate copolymers of either block or random nature. The polymers and copolymers may have structures that include backbone, side chains, graft, branch, hyperbranched, and/or dendritic. Examples of conjugated polymers that may be used, include, but are not limited to:

1. Poly(arylenes) include polyphenylenes, polyfluorenes, and polyanthracenes. Hydrocarbon aromatic polymers that have high efficiency of light emission may also be used.
2. Poly(arylene vinylene)s including aromatic hydrocarbon arylenes such as poly(phenylene vinylene), poly (anthracenylene vinylene) and other aryl linked vinylene-based polymers. Hydrocarbon vinylene-based polymers that have a high efficiency of light emission may also be used. Poly(arylene vinylene)s where the arylene unit is heterocyclic in nature, including poly (thienylene vinylene) and/or poly(pyridine vinylene), known for their red-shifted luminescence relative to PPV's and oxadiazole-containing polymers, known for their enhanced electron transport carrying capabilities.
3. Poly(heterocycle)s including poly(thiophene)s, known for their enhanced hole transporting capabilities and poly(furans).

All of the polymer families can be functionalized to provide processability through solubility and fusibility. Substituent groups include but are not limited to alkyl, alkyl ether, oligoether, alkyl sulfonate, alkyl amine, and other groups.

Figure 3:
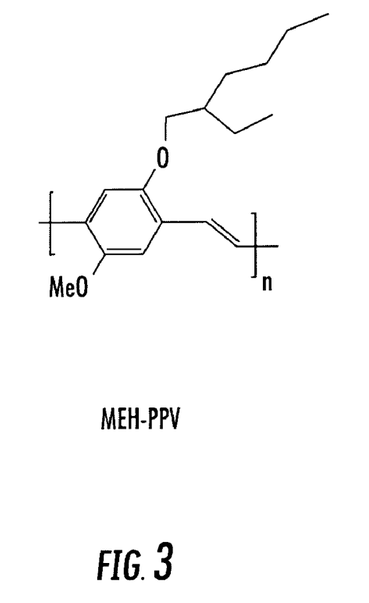
FIG. 3 is a schematic diagram of the chemical structure of MEH-PPV.
Figure 4:
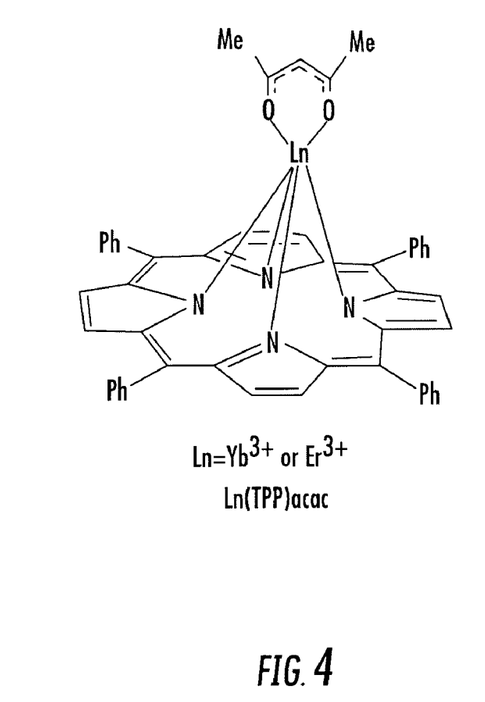
FIG. 4 is a schematic diagram of the chemical structure for Ln(TPP)acac.

Near-IR photoluminescence (PL) and/or electroluminescence (EL) can be achieved from blends of MEH-PPV with Yb(TPP)acac and/or Er(TPP)acac. FIG. 3 shows the structure for MEH-PPV and FIG. 4 shows the structure for Ln(TPP)acac, where $Ln=Yb^{3+}$, TPP=5, 10, 15, 20-tetraphenylporphyrin, and acac=acetylacetonate. These materials may involve sensitization of a lanthanide-TPP complex by a conjugated polymer, which can lead to the narrow bandwidth emission derived from, for example, $Yb^2F_{7/2} \to {}^2F_{7/2}$ (977 nm) and/or $Er^{4} I_{15/2} \to I_{15/2}$ (1560 nm) transitions. A varie lanthanides may be used to provide tunable PL and EL throughout the near-IR region. For instance, Yb- and Er-TPP (acac) complexes can provide emission at 977 nm and 1560 nm, respectively.

The efficiency of the luminescence from lanthanides may be increased by complexing the ions with a ligand-chromophore that can serve to more efficiently harvest the energy and sensitize the lanthanide's emission, for example, by exchanging energy transfer from the ligand-based triplet state. The TPP ligand has a high degree of spectral overlap of its Q-absorption bands with the MEH-PPV fluorescence allowing, for example, highly efficient Förster energy transfer. Due to the excellent spectral overlap, addition of Yb(TPP)acac or Er(TPP)acac to MEH-PPV can lead to efficient quenching of the fluorescence from the conjugated polymer host. Furthermore, in lanthanide porphyrin complexes, intersystem crossing to the triplet state can occur with high efficiency, which may approach 100% in some embodiments. The ligand can also act as an effective sensitizer to produce the spin-forbidden, luminescent F-states of the lanthanide ions.

Figure 5:
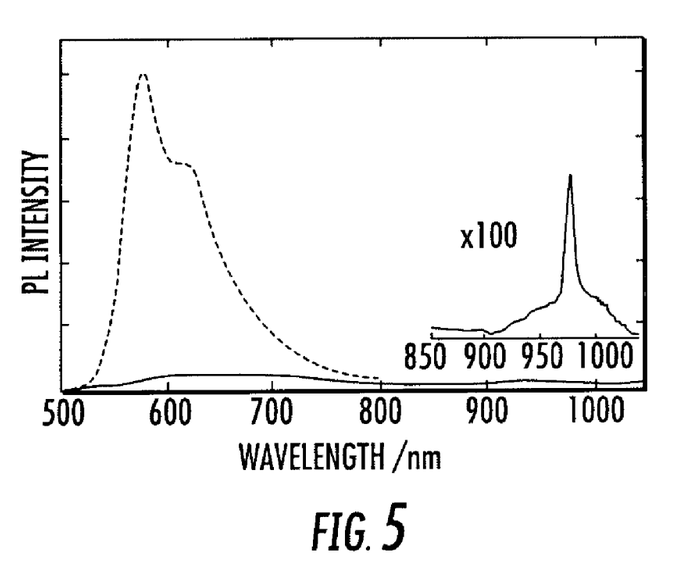
FIG. 5 shows an EL spectrum of MEH-PPV doped with 5 mol % Yb(TPP)acac measured at 9V and of MEH-PPV doped with 5 mol % Er(TPP) acac at 13V.

The electroluminescence material may be formed from a 100 nm thick spin-coated film produced by blending Yb(TPP)acac or Er(TPP)acac with MEH-PPV. FIG. 5 illustrates the photoluminescence of neat MEH-PPV (–) and MEH-PPV doped with 2 mol % Yb(TPP)acac (–)(based on polymer repeat unit), upon excitation at 350 nm. The spectrum of the blend is plotted on the same absolute scale as that of the neat polymer, with the y-scale of the inset expended by a factor of 100. The MEH-PPV fluorescence that appears at 589 nm is quenched approximately 98% when Yb(TPP)acac is present. Quenching of the visible emission may be accompanied by the appearance of the Yb emission at 977 nm in the near-IR. An excitation spectrum for the 977 nm emission shows a strong band that is due to the visible absorption of the host polymer, demonstrating its role as a sensitizer. Analogous results can be observed when Er(TPP)acac is blended into MEH-PPV, with the near-IR emission appearing at 1560 nm.

In at least one embodiment, the near-IR electroluminescent light source may be formed from an indium-tin-oxide (ITO) glass coated with PEDOT/PSS (Bayer Baytrom P VP Al 4083) as a hole transport layer. The MEH-PPV:Ln(TPP) acac blend may be spin coated from solution (1% wt of the polymer in toluene) and the resulting film vacuum dried from 12 hours ($1 \times 10^{-6}$ torr) at room temperature. Calcium (50 Å) followed by Al (1500 Å) layers may then be thermally evaporated at $1 \times 10^{-6}$ Torr without breaking the vacuum between the metal depositions. After deposition, the light source may be encapsulated with epoxy to minimize exposure to oxygen and moisture.

The light source 12 may also be a light source for phototherapy or photodynamic therapy that can be positioned in close proximity to or in direct contact with the tissue or skin of the patient. In certain embodiments consistent with the present invention, the light source has a thin, lightweight TFEL panel designed to provide uniform illumination over the area to be treated without the use of diffusers that would attenuate a portion of the light output. A single illuminating unit can be used as a TFEL panel requiring only two electrodes with two electrical connections, and can be made as large as several inches by several inches or even several feet by several feet. The light source may be operated in a range of power and frequency that does not generate excessive heat so that the light source surface may be used in contact with a patient's skin without discomfort and without need for the use of a cooling mechanism. The light source can be designed to emit light with wavelengths ranging from the visible to the infrared range. Selection of the appropriate wavelength allows the optimization of the light source for specific treatments.

Figure 6:
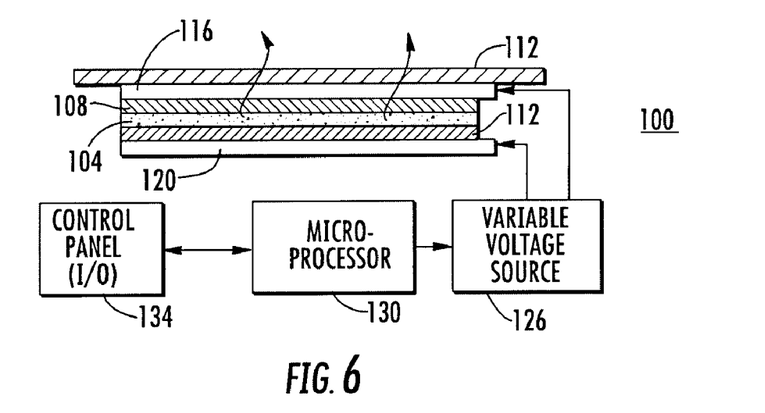
FIG. 6 is a cross-sectional view of a thin film electroluminescent light source.

As shown in FIG. 6, an exemplary TFEL panel and associated circuitry consistent with certain embodiments of the present invention is illustrated as 100. For purposes of the current discussion, start by assuming that this is an inorganic high field EL device. In this simple embodiment, a thin film electroluminescent panel is fabricated by sandwiching an inorganic electroluminescent layer 104 between two transparent insulators 108 and 112, which are further sandwiched between a pair of electrodes 116 and 120. The seal material (glass or polymer) 122 covers the light emitting portion of the device and protects the user from the high voltage used to generate the light. In one embodiment, the layer 122 also serves as a substrate for the growth of thin films of the materials composing the TFEL panel. When layer 122 serves only as a seal material, the substrate supporting the thin films can be placed beneath the bottom electrode 120. This produces a single illuminating unit requiring only two electrodes that can be as large as several inches by several inches and even several feet by several feet.

In this exemplary embodiment, an active inorganic electroluminescent layer 104 generates light by impact excitation of a light-emitting center (called the activator or dopant), embedded in a host material, by high-energy electrons. Since the electrons gain their energy from an electric field (1-2 MV/cm), this type of EL is often called high field electroluminescence (HFEL). A host matrix with an activator in this embodiment can be in the form of inorganic thin film or powder doped with a metal ion (ions) or metal complex (complexes). In general, the host material has a band gap large enough to emit light without absorption as well as to provide a medium for the efficient transport of high energy electrons. Examples of the inorganic host matrix forming the electroluminescent layer include, but are not limited to, ZnS, SrS, $ZnGa_2O_4$, $ZnSiO_4$, CaSSe, CaS and others. Examples of active centers incorporated in the EL phosphor material include, but are not limited to: Mn, Cu, rare earth elements (such as Ce, Nd, Sm, Eu, Tb, Tm, Er, Nd and others), and their complexes (TbOF and others). The electroluminescent layer 104 may be formed from ZnS, SrS, or an oxide layer doped with the above-identified EL phosphor material.

To enhance the efficiency and shift the peak emission wavelength, co-doping can be also used (for example, Ag in SrS:Cu with Ag in SrS for a blue EL phosphor). The insulators 108 (for example, ATO, which is a mixture of $TiO_2$ and $Al_2O_3$) and 112 (for example, barium tantalate, which is $BaTa_2O_4$) on either side of the active layer limit the maximum current to the capacitive charging and discharging displacement current level. The insulators 108, 122 may also be formed from silicon oxynitride Electrodes sandwiching the insulator and EL layers form a basic capacitive structure. Electrode 116 is a transparent conductive electrode such as, for example, an Indium Tin Oxide (ITO) electrode or aluminum, that permits light of a certain wavelength range to pass. Alternate electrode materials, such as nickel-cobalt spinel oxide, may be used to extend the range of transparency further into the IR range.

Electrode 120 is preferably somewhat reflective (for example, Al) so that light that is incident on electrode 120 will reflect back through electrode 116. In certain embodiments consistent with the present invention, the electrode closer to the area to be treated by the TFEL light source is transparent while the second electrode serves as a reflector. Light emitted in the phosphor layer is uniform in all directions. The reflecting electrode serves to reflect light generated in the phosphor layer emitted in that direction as well as any light reflected from the patient's skin not absorbed by the other layers in the TFEL structure. Due to the reflective properties of the electrode, the overall light source efficiency is improved. The highest luminance reported in flat panel display industry for TFEL panel (pixelated) with inorganic emission layer in the visible region of light spectrum currently is >1000 cd/m$^2$ (>1 mW/cm$^2$).

A typical thickness of the TFEL panel, not counting a substrate, is about 1.5 mm. A typical thickness of a glass or polymer substrate in an EL device is about 1 mm. Thus the illuminating panel can be made to be very light and compact. This structure can be extended in width to produce a TFEL panel that is large in area and somewhat planar with a very thin cross section. Yet wiring to such a device may remain as simple as a two-wire connection.

In another embodiment, the active layer of the TFEL is an organic-based material. Organic-based electroluminescent light (OEL) sources have been under development for several years and may be particularly attractive for PT applications because of their very simple fabrication techniques (for example, spin on coating of organic material), high brightness emission in the visible and IR part of the spectrum and low operational voltage. The high brightness makes OEL displays attractive as a source of radiation and the low voltage operation allows the OEL sources to be battery powered, which enhances their portability and ease of use in the field.

FIG. 6 can also represent the structure of an OEL. In this case, the active layer 104 is an organic material as will be described later. The electrodes 116 and 120 are similar or identical in structure to that of the inorganic HFEL source previously described. Instead of insulating layers 108 and 112, the OEL often uses an electron/(or hole) injection/(or blocking) layer that is similarly located. Additionally, the organic material forming the active layer may be made up of multiple layers and may or may not have a dopant.

Currently, the typical luminance of OEL sources is between several hundred $cd/m^2$ to several thousand $cd/m^2$. However, luminance as large as slightly less than 40000 $cd/m^2$ (corresponding to about 40 $mW/cm^2$) in the region of visible light has been observed. A large variety of polymers, copolymers and their derivatives have been demonstrated within last the decade to posses EL properties. The configuration of such polymer-based devices may have a simple single layer, bilayers, or blends of polymers used to enhance efficiency, tune the emission wavelength or even provide devices that emit light of different colors simply by changing the driving voltage. In the last case, as an example, a blend of two polythiophene-based polymers can be cited, which posses two different bandgaps and thus different emission colors and different turn-on voltages. As described above, a typical single layer polymer organic TFEL is constructed by sandwiching a thin layer of luminescent conjugated polymer between an anode and cathode, where one electrode is transparent. Organic materials can be also be made up of emitting metal containing organic compounds (for example, aluminum, tris(8-hydroxyquinoline, and conjugated polymers)) incorporated into the polymer host matrix also have been employed as OEL materials for generating visible light. When containing rare earth ions, emission from metal containing organic compounds often exhibit sharp peaks in both visible and NIR spectral regions. Relatively recently, organolanthanide phosphors have been demonstrated to give high enough brightness and efficiency to underline their potential for use in OEL devices. Organic TFEL devices are sometimes referred to as an OLED.

In one embodiment consistent with the present invention, organic-based TFEL panel 100 has a layer 122 that forms a supporting substrate (glass or polymer) and that also serves as a sealing material protecting the organic material from degradation, a transparent conducting electrode 116 (such as, for example, ITO), a hole transport conducting polymer layer 108 (such as, for example PEDOT-PSS), the active light emitting layer 104, and the top electrode structure in the form of a calcium layer 112 and aluminum layer 120, where Ca and Al can be substituted by other conductive materials with relatively low work function. The emitting layer can be, for example, made of blends of MEH-PPV or PPP-OR11 with lanthanide-TPP complexes, where lanthanide can be Yb (peak emission at 977 nm), Er (1560 nm) and others.

In another embodiment, the OEL device emitting red light (612 nm peak) can have the following layers: glass (polymer) substrate/ITO/Eu(TTFA)3(phen):PBD:PVK/BCP/Ca/Al. In this embodiment, a new functional layer—BCP, is incorporated as a hole-blocking layer substantially improving brightness and efficiency. In general, in addition to the layers of materials described above, additional layers for OEL device can be incorporated, such as electron or hole injection or blocking layers. Other configurations are also possible without departing from the present invention.

In both inorganic and organic-based TFEL devices, a single emitting unit driven by two electrodes can be substantially large due to much lower current generated in these structures as compared to semiconductor LEDs. A single illuminating unit requires only two electrodes but can be as large as several inches by several inches and even several feet by several feet. The current within high field inorganic EL and OELs range from several $mA/cm^2$ to about 100 $mA/cm^2$, while for semiconductor LEDs it is about 100 $A/cm^2$.

Light is generated in inorganic TFEL device 100 by application of an AC voltage across electrodes 116 and 120 of sufficient magnitude to cause emission of light by the active layer 104. DC could be used but at the expense of higher current drain. Electrical charge is injected into the active layer, by application of voltage across the electrodes, exciting the dopant atoms. Relaxation of the dopant atoms back to the ground state results in the emission of photons characteristic of the dopant atom and the phosphor host. The wavelength of the light emitted is determined by the dopant or dopants in the active layer. Each dopant used in the TFEL panel will exhibit a unique spectral output characteristic of that dopant. Often, if a single dopant is used, light will be emitted predominantly at a single wavelength, but often a single dopant will also result in multiple dominant lines in the output frequency spectrum. Multiple dopants, such as, but not limited to three, can be effectively used to generate light at multiple wavelengths or spectra.

Inorganic TFEL devices have been optimized for emission in the visible wavelength range specifically for display applications using, for example dopants such as copper to produce blue emission and manganese to produce amber emission. Doping the phosphor layer with a rare-earth element, a strong EL emission band produces light in the infrared range accompanied in many cases by some level of emission in the visible range. The selection of the appropriate dopant allows the characteristic EL emission to be changed to wavelengths ranging from the visible to the infrared. The spectrum can also be modified somewhat by annealing. The emission is determined by the specific dopant used. The use of two or more dopants can produce multiple characteristic emission lines. The wavelengths may be chosen to match the portions of the electromagnetic spectrum known to have therapeutic benefit in phototherapy, or to activate the photoreactive agent in photodynamic therapy. Some illustrative dominant wavelengths associated with several dopants are given by Table 1 below. This listing should not be considered exhaustive or limiting, but merely illustrative of the ability to produce EL emissions in the range of wavelengths that are useful for phototherapy applications.

TABLE 1

| INORGANIC AND ORGANIC EL MATERIAL (MATRIX:DOPANT) | DOMINANT LIGHT WAVELENGTHS EMITTED FROM EL SOURCE |
| --- | --- |
| ZnS:Tm (Thulium) | 480 nm and 800 nm |
| ZnS:Nd (Neodymium) | 890 nm |
| ZnS:Er (Erbium) | 550, 660 and 980 nm |
| ZnS:Mn | 580 nm (yellow) |
| SrS:Cu | 475 nm (green/blue) |
| (SrS:Cu, Ag) | (430 nm) (blue) |
| SrS:Ce | 510-550 nm double peaked |
| Eu(TTFA)$_3$(phen):PBD:PVK | 612 nm (red) |
| Yb(TPP)acac:MEH-PPV | 977 nm |

Light emitted from a TFEL source such as described herein is generally not a pure light at any given wavelength. Rather, the light source produces a spectrum of light that frequently exhibits sharp peaks in intensity at one or more wavelengths. The approximate wavelength of the dominant intensity peaks are listed in the table above for the exemplary dopants listed. Uniform light intensity over the entire light source surface area is achieved with uniform dopant distribution and film thicknesses in the TFEL panel, parameters readily controlled during the manufacturing process.

In the phototherapy device 100 of FIG. 6, a variable voltage source 126 supplies AC voltage to the TFEL panel electrodes 116 and 120 to induce emission of light. In this embodiment, the variable voltage source supplies a voltage under control of microprocessor 130. The microcontroller may control any one or more desired parameters of the AC voltage including, but not limited to, voltage level, frequency and modulation characteristics to control the light output from the TFEL panel. The desired output level and other parameters can be controlled by user input to a control panel 134 operating as a user interface providing I/O functions to the microprocessor 130. Such parameters may be directly controlled in some embodiments or controlled as a function of treatment selections made at the control panel without knowledge of the actual physical parameters being influenced.

In the embodiment illustrated, if multiple dopants are used and uniformly distributed, then light is emitted at multiple frequencies at a variable intensity level and time that is controllable by microprocessor 130 which acts as a controller upon appropriate receipt of user input at control panel 134. According to this design, the TFEL source can be manufactured and operated as a single light source with the entire panel uniformly activated. One or more conductive elements is attached to both the top and bottom electrode of the TFEL panel and connected to a suitable power source such as source 126. This simple design results in a reliable TFEL light source since there are minimal components and minimal connections, and produces a device that is light in weight with low heat generation and low current drain. In this embodiment, all available spectra of light from the TFEL panel are produced whenever an appropriate voltage is applied to the panel. For inorganic TFEL, a relatively high voltage (about 200V) may be required to produce light emissions. In this case, the voltage source 126 may incorporate a voltage converter to appropriately boost the voltage to required levels. However, it should be noted that high voltage does not imply limitations on portability. In addition, TFEL displays have superb shock resistance and can normally operate at $-25°$ C. to $+65°$ C.

Figure 7:
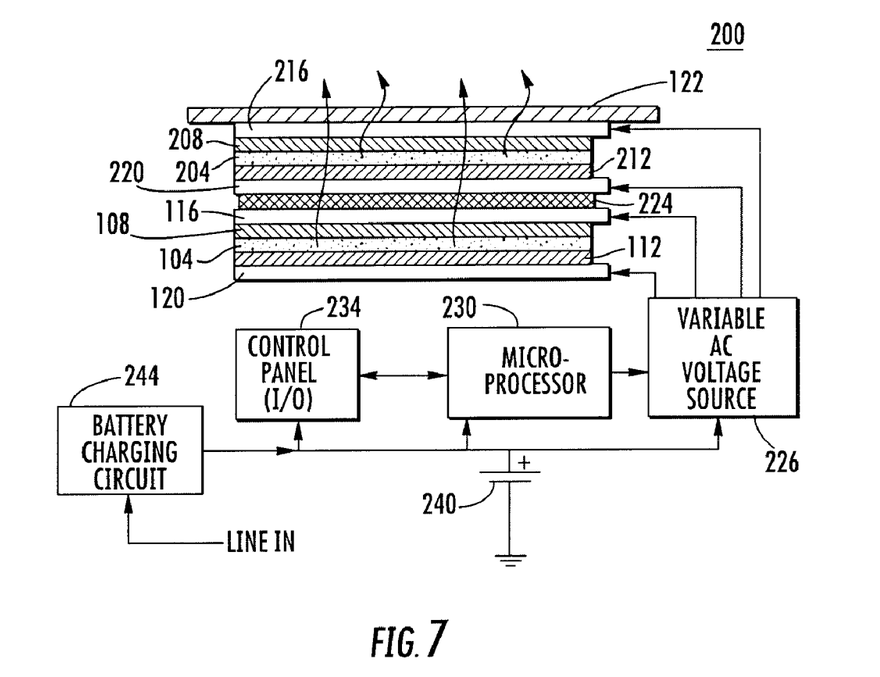
FIG. 7 is a cross sectional view of another thin film electroluminescent light source.

In an alternative embodiment, as illustrated in FIG. 7, a phototherapy device 200 is illustrated in which multiple light spectra are individually selectable. In this embodiment, two or more TFEL panels are stacked to provide the user with the ability to individually address each panel and thus select one of two wavelengths, or sets of wavelengths, for the phototherapy treatment protocol. For an inorganic TFEL, the first panel structure is similar to that of FIG. 6 in which the active layer 104, surrounded by insulators 108 and 112 are positioned between transparent electrode 116 and electrode 120 (Electrode 120 is preferably reflective at the wavelengths of interest.). A second TFEL panel is fabricated by positioning a second active layer 204 between two transparent insulators 208 and 212. The two transparent insulators 208 and 212 are in turn positioned between a pair of transparent electrodes 216 and 220. Electrode 220 is then coupled to electrode 116 using a transparent insulating glue or tape 224 or other mechanism to hold the two panels together. In another embodiment, a single electrode may be substituted for electrodes 220 and 116 by appropriate modification of the outputs from the variable voltage source. In an organic TFEL embodiment, the structural changes discussed in connection with FIG. 6 can be applied equally to the structure of FIG. 7 to achieve a multiple layer organic active layer TFEL.

In this embodiment, variable voltage source 226 supplies voltage across electrodes 116 and 120 and across electrodes 216 and 220. The device is again isolated from the user's skin by a seal layer 122. Thus, the light emission from the top panel and the bottom panel can be independently selected by selective application of voltage to the two stacked TFEL panels. Due to having to pass through the upper TFEL panel, emissions from the lower TFEL panel will be slightly attenuated compared to those from the upper TFEL panel, and this should be accounted for in development of treatment protocols. Since the thickness of each EL panel can be about 1 mm, the attenuation is generally low (about 10%). The output, as in device 100, is selected by controlling the variable voltage source 226 by microprocessor 230 operating under control of a computer program with the user input selected via control panel 234. Due to the low current consumption of the TFEL panel, this apparatus (as well as apparatus 100) may be readily battery powered by battery 240. Battery 240 can either be replaceable batteries or may be a rechargeable battery that can be charged by battery charging circuit 244. This circuit may also incorporate voltage regulators and voltage converters (for inorganic TFEL) and other peripheral circuitry as will be clear to those skilled in the art to assure uniformity of voltage, etc.

An alternate embodiment involves producing a patterned array of TFEL pixels in order to produce multiple characteristic emission lines. Some of the pixels are designed to emit one wavelength or spectrum while others are designed to produce an alternate wavelength or spectrum by doping the phosphor used to generate the two types of pixels with different dopants. The pixels can be interconnected so that all the pixels of one type can be activated simultaneously. The two, or more, pixel types could be switched on separately to generate emission characteristic of the activated pixels or rapidly switched on and off sequentially producing both types of emission.

Figure 8:
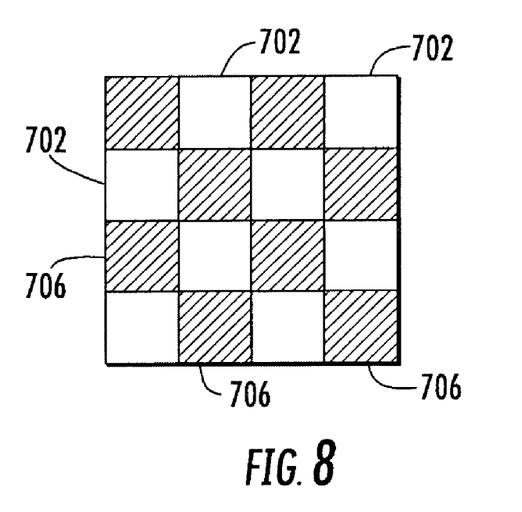
FIG. 8 is an exemplary pixel pattern for a first TFEL panel consistent with certain embodiments of the present invention.

FIG. 8 illustrates one embodiment that uses arrays of pixels in a prescribed pattern to produce multiple spectra of light emissions. In this embodiment, a checkerboard pattern is used with alternating segments of doped electroluminescent material being doped with two different dopants. For example, a first dopant can be used to dope segments 702 (represented by the white squares), while a second dopant can be used to dope segments 706 (represented by the hashed squares) in the same manner used to create pixels in a video display. In a case of organic TFEL based on light emitting polymers which do not require dopants, these segments can be made of different types of light emitting polymers. Electrodes are fabricated so that each of the segments 702 can be collectively addressed (again in a manner similar to that used in video displays, except that all pixels associated with each spectrum can be addressed simultaneously) and each of the segments 706 can be collectively addressed. The user can then address segments 702 with appropriate drive voltage to produce light at the wavelength associated with the dopant used in the segments associated with 702. The user can separately or simultaneously address the segments 706 associated with the second dopant to produce light having different spectral characteristics. As the segments are made smaller and smaller, the light from the panel becomes more uniform, but the panel becomes somewhat more complex and expensive to manufacture. Similarly, depending on applications, a TFEL panel with only one dopant can also be pixilated. The pixel size can range from several mm to several inches.

Figure 9:
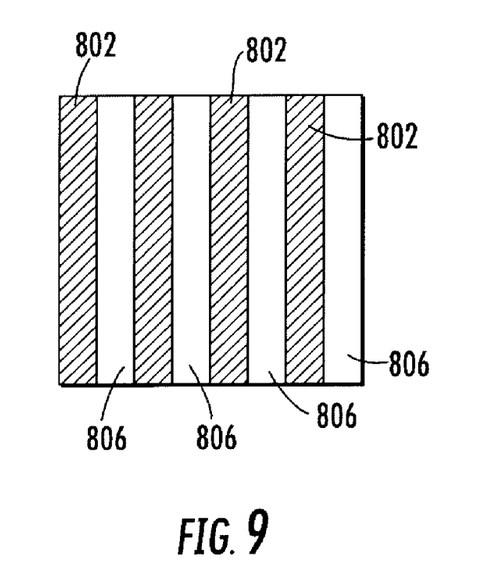
FIG. 9 is an exemplary pixel pattern for a second TFEL panel consistent with certain embodiments of the present invention.

A somewhat simpler structure is illustrated in FIG. 9 in which alternating segments of the panel with first and second dopants are fabricated in successive columns. Thus, a column 802 has the first dopant and the column 806 has the second dopant. Again, the complexity of manufacture increases as the columns are made smaller, but the uniformity of the output becomes better. Of course, those skilled in the art will appreciate that other arrangements of doped segments of the panel can be devised, and that the present invention is not limited to two such dopants. Moreover, multiple dopants can be used for each of the segments of the panel and multiple layers can be used with these embodiments without departing from the present invention.

In addition to the embodiments described in connection with FIGS. 8 and 9, multiple layers (similar to the embodiment shown in FIG. 7) can be used to generate the pixels with an upper layer contributing to a first spectrum and the lower layer contributing to the second layer with the pixels alternating with one another as in FIGS. 8 and 9 to provide the user with the option of selection of either of the two spectra.

As previously noted, a further aspect of the present invention is the ability to bring the light source 12, the TFEL panel, in direct contact with the skin without the necessity of a cooling device. Other light sources, such as LEDs, exhibit higher power dissipation than TFEL devices. LEDs often produce a significant amount of heat and may require a cooling mechanism. The TFEL light source 12 may feel warm when in contact with the skin under normal operating conditions, but does not produce enough heat to require supplemental cooling. The TFEL light source 12 can be comfortably and safely used for extended periods of time.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A phototherapeutic bandage, comprising:
   a base formed from a flexible substrate;
   a thin film flexible electroluminescent source coupled to the base and extending continuously across at least a portion of the base for emitting radiation to a target area on a patient;
   wherein the bandage is capable of conforming to a surface area of the target area; and
   wherein said electroluminescent source is an inorganic electroluminescent source and comprises an electroluminescent layer positioned between two transparent insulators, wherein the two transparent insulators are positioned between two electrodes.

2. The phototherapeutic bandage of claim 1, wherein the two transparent insulators are selected from the group consisting of ZnS, SrS, $ZnGa_2O_4$, $ZnSiO_4$, CaSSe, CaS, and silicon oxynitride.

3. The phototherapeutic bandage of claim 1, wherein the two transparent insulators are selected from the group consisting of ATO and barium tantalate.

4. The phototherapeutic bandage of claim 1, wherein the electroluminescent layer is selected from the group consisting of Mn, Cu, Ce, Nd, Sm, Eu, Tb, Tm, Er, and Nd and as sulfides, halide compounds and complexes such as oxycompounds.

5. The phototherapeutic bandage of claim 1, wherein the electroluminescent layer is selected from the group consisting of Ag in SrS, and Cu with Ag in SrS for a blue EL phosphor.

6. The phototherapeutic bandage of claim 1, wherein the two electrodes are selected from the group consisting of aluminum, indium tin oxide and nickel-cobalt spinel oxide.

7. The phototherapeutic bandage of claim 1, wherein the electroluminescent layer is pixilated and capable of producing radiation in a plurality of narrowband wavelengths.

8. The phototherapeutic bandage of claim 1, wherein said inorganic electroluminescent source comprises zinc sulfide doped with at least one lanthanide.

9. A phototherapeutic bandage, comprising:
   a base formed from a flexible substrate;
   a thin film flexible electroluminescent source coupled to the base and extending continuously across at least a portion of the base for emitting radiation to a target area on a patient;
   wherein the bandage is capable of conforming to a surface area of the target area; and
   wherein said electroluminescent source is an organic electroluminescent source and comprises an electroluminescent layer positioned between two electron injection layers, wherein the two electron injection layers are positioned between two electrodes.

10. The phototherapeutic bandage of claim 9, wherein said electroluminescent layer is selected from the group consisting of aluminum, conjugated polymers, and organolanthanide phosphor.

11. The phototherapeutic bandage of claim 9, wherein the electroluminescent layer is pixilated and capable of producing radiation in a plurality of narrowband wavelengths.

12. The phototherapeutic bandage of claim 9, wherein the electroluminescent layer is formed from two or more layers.

13. A phototherapeutic bandage, comprising:
   a base formed from a flexible substrate;
   a thin film flexible electroluminescent source coupled to the base and extending continuously across at least a portion of the base for emitting radiation to a target area on a patient;
   wherein the bandage is capable of conforming to a surface area of the target area; and
   wherein said electroluminescent source is formed from a luminescent polymer and a metal containing compound, wherein the metal containing compound comprises a metal-ligand complex, wherein the adsorption spectrum of the metal-ligand complex at least partially overlaps with the emission spectrum of the luminescent polymer such that when the luminescent polymer becomes electronically excited, energy is transformed from the luminescent polymer to the metal-ligand complex, wherein at least a portion of the energy transferred from the luminescent polymer to the metal-ligand complex is emitted by the metal-ligand complex as near-infrared radiation.

14. The phototherapeutic bandage of claim 13, wherein the metal containing compound is a metal organic compound.

15. The phototherapeutic bandage of claim 14, wherein the metal organic compound comprises a lanthanide.

16. The phototherapeutic bandage of claim 13, wherein the metal organic compound comprises a lanthanide.

17. The phototherapeutic bandage of claim 16, wherein the luminescent polymer is MEH-PPV.

18. The phototherapeutic bandage of claim 13, wherein the luminescent polymer is a conjugated polymer.

19. The phototherapeutic bandage of claim 13, wherein the metal-ligand complex is Ln(TPP)acac, where Ln is selected from the group consisting of $Yb^{+3}$, $Er^{+3}$, Nd, Dy, and Tm.

20. A phototherapeutic bandage, comprising:
a base formed from a flexible substrate;
an adhesive layer having a first and second side, wherein the first side of the adhesive layer is attached to the base and the second side is for fastening said bandage to a target area on a patient;
a single, continuous, thin film, flexible electroluminescent source coupled to the base and extending continuously across at least a portion of the base for emitting radiation to the target area on a patient;
wherein the bandage is capable of conforming to a surface area of a body to be treated;
wherein the electroluminescent source is capable of producing near-infrared light; and
wherein said electroluminescent source is an inorganic electroluminescent source and comprises an electroluminescent layer positioned between two transparent insulators, wherein the two transparent insulators are positioned between two electrodes.

21. The phototherapeutic bandage of claim 20, wherein the electroluminescent layer is selected from the group consisting of ZnS, SrS, $ZnGa_2O_4$, $ZnSiO_4$, CaSSe, and CaS.

22. The phototherapeutic bandage of claim 20, wherein the two transparent insulators are selected from the group consisting of ATO, barium tantalate and silicon oxynitride.

23. The phototherapeutic bandage of claim 20, wherein the electroluminescent layer is selected from the group consisting of a ZnS, SrS, and an oxide layer doped with Mn, Cu, Ce, Nd, Sm, Eu, Tb, Tm, Er, Nd, TbOF, Ag, and mixtures thereof.

24. The phototherapeutic bandage of claim 20, wherein the two electrodes are selected from the group consisting of aluminum, indium tin oxide and nickel-cobalt spinel oxide.

25. The phototherapeutic bandage of claim 20, wherein the electroluminescent layer is pixilated and capable of producing radiation in a plurality of narrowband wavelengths.

26. The phototherapeutic bandage of claim 20, wherein said inorganic electroluminescent source comprises zinc sulfide doped with at least one lanthanide.

27. A phototherapeutic bandage, comprising:
a base formed from a flexible substrate;
an adhesive layer having a first and second side, wherein the first side of the adhesive layer is attached to the base and the second side is for fastening said bandage to a target area on a patient;
a single, continuous, thin film, flexible electroluminescent source coupled to the base and extending continuously across at least a portion of the base for emitting radiation to the target area on a patient;
wherein the bandage is capable of conforming to a surface area of a body to be treated;
wherein the electroluminescent source is capable of producing near-infrared light; and
wherein said electroluminescent source is an organic electroluminescent source and comprises an electroluminescent layer positioned between two electron injection layers, wherein the two electron injection layers are positioned between two electrodes.

28. The phototherapeutic bandage of claim 27, wherein said electroluminescent layer is selected from the group consisting of aluminum, conjugated polymers and organolanthanide phosphor.

29. The phototherapeutic bandage of claim 27, wherein the electroluminescent layer is pixilated and capable of producing radiation in a plurality of narrowband wavelengths.

30. The phototherapeutic bandage of claim 27, wherein the electroluminescent layer is formed from two or more layers.

31. A phototherapeutic bandage, comprising:
a base formed from a flexible substrate;
an adhesive layer having a first and second side, wherein the first side of the adhesive layer is attached to the base and the second side is for fastening said bandage to a target area on a patient;
a single, continuous, thin film, flexible electroluminescent source coupled to the base and extending continuously across at least a portion of the base for emitting radiation to the target area on a patient;
wherein the bandage is capable of conforming to a surface area of a body to be treated;
wherein the electroluminescent source is capable of producing near-infrared light; and
wherein said electroluminescent source is formed from a luminescent polymer and a metal containing compound, wherein the metal containing compound comprises a metal-ligand complex, wherein the adsorption spectrum of the metal-ligand complex at least partially overlaps with the emission spectrum of the luminescent polymer such that when the luminescent polymer becomes electronically excited, energy is transformed from the luminescent polymer to the metal-ligand complex, wherein at least a portion of the energy transferred from the luminescent polymer to the metal-ligand complex is emitted by the metal-ligand complex as near-infrared radiation.

32. The phototherapeutic bandage of claim 31, wherein the metal containing compound is a metal organic compound.

33. The phototherapeutic bandage of claim 32, wherein the metal organic compound comprises a lanthanide.

34. The phototherapeutic bandage of claim 31, wherein the metal organic compound comprises a lanthanide.

35. The phototherapeutic bandage of claim 34, wherein the luminescent polymer is MEH-PPV.

36. The phototherapeutic bandage of claim 31, wherein the luminescent polymer is a conjugated polymer.

37. The phototherapeutic bandage of claim 31, wherein the metal-ligand complex is Ln(TPP)acac, where Ln is lanthanide element selected from the group consisting of $Yb^{+3}$, $Er^{+3}$, Nd, Dy, and Tm.

* * * * *